United States Patent [19]

Farber et al.

[11] Patent Number: 4,856,073

[45] Date of Patent: * Aug. 8, 1989

[54] AUTOMATED MICROBIOLOGICAL TESTING APPARATUS AND METHOD

[75] Inventors: Glenn L. Farber, Port Jefferson; Maria C. Navarro, North Massapequa, both of N.Y.

[73] Assignee: Sherwood Medical Company, St. Louis, Mo.

[ * ] Notice: The portion of the term of this patent subsequent to Feb. 9, 2005 has been disclaimed.

[21] Appl. No.: 118,917

[22] Filed: Nov. 10, 1987

Related U.S. Application Data

[62] Division of Ser. No. 706,068, Feb. 27, 1985, Pat. No. 4,724,215.

[51] Int. Cl.$^4$ .............................................. G06K 9/00
[52] U.S. Cl. ........................................ 382/6; 356/72; 356/246; 356/419; 364/497; 382/1; 422/67; 435/291
[58] Field of Search ............... 356/39, 72, 73, 244, 356/246, 416, 419, 440; 364/413, 415, 416, 496, 497, 498, 499; 422/58, 59, 60, 63, 67, 68.08; 436/43; 435/287, 289, 291, 300, 301; 382/1, 6, 9, 13, 69; 358/139

[56] References Cited

U.S. PATENT DOCUMENTS

| | | | |
|---|---|---|---|
| 3,999,047 | 12/1976 | Green | 382/6 |
| 4,038,151 | 7/1977 | Fadler et al. | 435/101 |
| 4,061,469 | 12/1977 | DuBose | 422/67 |
| 4,166,095 | 8/1979 | Kling et al. | 422/67 |
| 4,191,940 | 3/1980 | Polcyn et al. | 356/39 |
| 4,193,694 | 3/1980 | Smith | 356/419 |
| 4,358,203 | 11/1982 | Citrin | 435/287 |
| 4,400,353 | 8/1983 | Meserol et al. | 422/58 |
| 4,453,220 | 6/1984 | Flegal et al. | 364/497 |
| 4,580,895 | 4/1986 | Patel | 356/39 |
| 4,634,576 | 1/1987 | Galle et al. | 356/246 |
| 4,676,951 | 6/1987 | Armes et al. | 435/301 |
| 4,678,894 | 7/1987 | Schafer | 364/416 |
| 4,684,244 | 8/1987 | Butts et al. | 356/440 |
| 4,720,463 | 1/1988 | Farber et al. | 422/65 |
| 4,724,215 | 2/1988 | Farber et al. | 358/139 |

Primary Examiner—Leo H. Bourdreau
Assistant Examiner—Jose L. Couso
Attorney, Agent, or Firm—Stanley N. Garber; Andrew J. Beck; William R. O'Meara

[57] ABSTRACT

Apparatus for obtaining test results from microbiological test trays and strips includes an inspection station of which test trays may be inspected to determine the results of microbiological tests, a video camera disposed to form images of the test trays at the inspection station, and an image processor for receiving the images from the video camera and processing them to determine test results. Only predetermined areas of interest in the image made by the camera are electronically analyzed. Each well of a given tray is assigned a positive or negative partial result based upon the electronic analysis of the area or areas of interest within that well.

22 Claims, 9 Drawing Sheets

AUTOMATED MICROBIOLOGICAL TESTING APPARATUS AND METHOD

This is a divisional of co-pending application serial no. 706,068 filed on Feb. 27, 1985, now U.S. Pat. No. 4,724,215.

BACKGROUND OF THE INVENTION

This invention relates to microbiological testing apparatus and methods, and more particularly to an improved system for facilitating the automatic incubation and reading of microbiological test trays.

A number of different types of microbiological testing are carried out in trays or strips (referred to herein collectively as "trays") which have a number of chambers known as test wells or cupules. Such trays are used, for example, to identify a microorganism, or to determine the susceptibility of that organism to a number of antimicrobics, which latter trays are called susceptibility trays. Typically, the test wells or cupules in the identification trays contain complex chemicals or reagents which in the presence of an active fermenting culture change color, become cloudy or otherwise indicate that fermentation is or has taken place. Similarly, in one known susceptibility test called the minimum inhibiting concentration (MIC) test, the wells contain different dilutions of various antimicrobics and a growth medium to determine the dilution level of the antimicrobic which is sufficient to kill and/or inhibit growth of the organism.

Conventionally, the test reagents and any growth medium or antimicrobics are placed into the test wells in the form of an aqueous solution and later lyophilized. A different combination of reagent or growth medium is charged into different wells so that a great number of individual reactions are performed in a physically small apparatus. For example, in the MIC tests, a regular pattern of wells arranged in rows and columns could be provided, each row of wells containing different antimicrobics. Within a row, the concentration of the antimicrobic would increase from well to well by a factor of, for example, 2. Of course, other dilution ratios could be used.

When a test is to be performed, a microorganism is innoculated into each of the test chambers with sufficient water to reconstitute the reagents. The test trays are then incubated at an appropriate temperature, such as 35-37 degrees Celsius for an extended period of time. After a predetermined period, the individual chambers are examined for the presence or absence of a reaction or indication of color change, or a change in turbidity. Heretofore, it is believed that the inspection of the wells for the presence or absence of a reaction or indication was done manually at least in part. Thus, individual trays each required the use of technician's time in the preparation, innoculation, incubation and reading of the results. Moreover, since different test trays might be needed to determine different characteristics of the microorganisms, the reading of a variety of different trays could be a fairly complex proceedure.

Systems have been provided for automating at least a portion of the reading process. In one existing system for use in semi-automatically recording the results of microbiological tests, a test tray having a plurality of test wells arranged in a certain pattern is placed beneath a transparent keyboard. A light source projects light through the tray and the keyboard so that the user can view the tray with its test wells through the keyboard. The keys of the keyboard correspond to the test wells, so that the user presses the keys overlying those wells in which the certain test results have occurred in order to record the results of the tests conducted in the test wells. Such a method of reading the test wells requires a highly skilled technician and a good deal of technician's time. In addition, the incubation times for identification and susceptibility trays may be quite different, with the result that the user will be recording the results for a particular patient or specimen at two different times, with the possibility that the identification and susceptibility results might not be properly assigned to the same patient. Moreover, the difference in times of incubation for identification and susceptibility trays means that the user or operator must return twice to the incubator for each patient.

SUMMARY OF THE INVENTION

Among the various aspects and features of the present invention may be noted the provision of an apparatus for automating the microbiological test procedure from incubation through the actual reading of the test tray itself; the provision of such an apparatus which eliminates to a large extent the necessity of having a highly trained technician read test results; the provision of such an apparatus which insures that identification and susceptibility results for the same patient remain together; the provision of such an apparatus which is compatible with currently available identification and susceptibility test trays; the provision of such an apparatus that is flexible enough to use with a number of different tray combinations; and the provision of such an apparatus which is relatively economical to use.

Other aspects and features of the present invention will be in part apparent and in part pointed out hereinafter.

Briefly, in a first aspect an automated microbiological testing apparatus of the present invention includes an incubation chamber for incubating a plurality of microbiological test trays such as susceptibility trays and identification trays, an inspection station at which the test trays may be inspected to determine the results of the microbiological tests, means for moving any predetermined test trays desired from the incubation chamber to the inspection station, and means for processing the image of the test tray at the inspection station to determine test results.

In a second aspect of the invention, an automated microbiological testing apparatus includes an incubation chamber for incubating a plurality of microbiological test trays such as susceptibility trays and identification trays, an inspection station at which the test trays may be inspected by the apparatus to determine the results of microbiological tests, means for moving any predetermined test trays desired from the incubation chamber to the inspection station, and means for automatically determining test results at the inspection station.

In a third aspect of the present invention, a carrier for a microbiological tray includes a relatively rigid frame defining at least one central opening suitable for holding and supporting a microbiological tray, the tray having a pair of opposed, parallel shoulders suitable for riding on a pair of parallel rails, and receiving means integrally formed in the frame by means of which an external driving force may be applied to the frame to move it along the rails.

In a fourth aspect of the present invention, a diagnostic microbiological testing apparatus for obtaining test results from microbiological test trays and strips such as susceptibility trays and identification trays, each tray having a plurality of wells, comprises an inspection station at which the test trays may be inspected to determine the results of the microbiological tests, a video camera disposed to form images of the test trays at the inspection station, and processing means for receiving the images from the video camera and processing them to determine test results.

In a fifth aspect of the present invention, a method of automatically reading the results from microbiological test trays and strips such as susceptibility trays and identification trays, each tray having a plurality of wells, comprises the steps of making an image with a video camera of a tray to be read, electronically analyzing only predetermined areas of interest in the image made by the camera, which areas of interest are substantially within the outlines of the tray wells in the image, electronically determining for each well of interest the number of pixels in each area of interest having an associated value that extends a predetermined threshold for that area of interest, and electronically assigning a binary partial result to each well based upon the number of pixels which exceeded the predetermined threshold for each corresponding area of interest.

In a sixth aspect of the present invention, a method of automatically reading the results from microbiological test trays and strips such as susceptibility trays and indentification trays comprises the steps of moving a tray to be read to an inspection station, and electronically reading the tray at the inspection station with a camera which remains substantially stationary with respect to the tray while the reading of the tray is occurring.

BRIEF DESCRIPTION OF THE DRAWINGS

FIG. 15 is a perspective of the reagent reservoir of the apparatus of the present invention;

FIG. 16 is a schematic of carrier presence sensing apparatus of the present invention;

FIG. 17 is a schematic of elevator position sensing apparatus of the present invention; and FIG. 18 is a schematic of carrier position sensing apparatus of the present invention.

Similar reference characters indicate similar parts throughout the several views of the drawings.

DESCRIPTION OF THE PREFERRED EMBODIMENT

Figure 1:
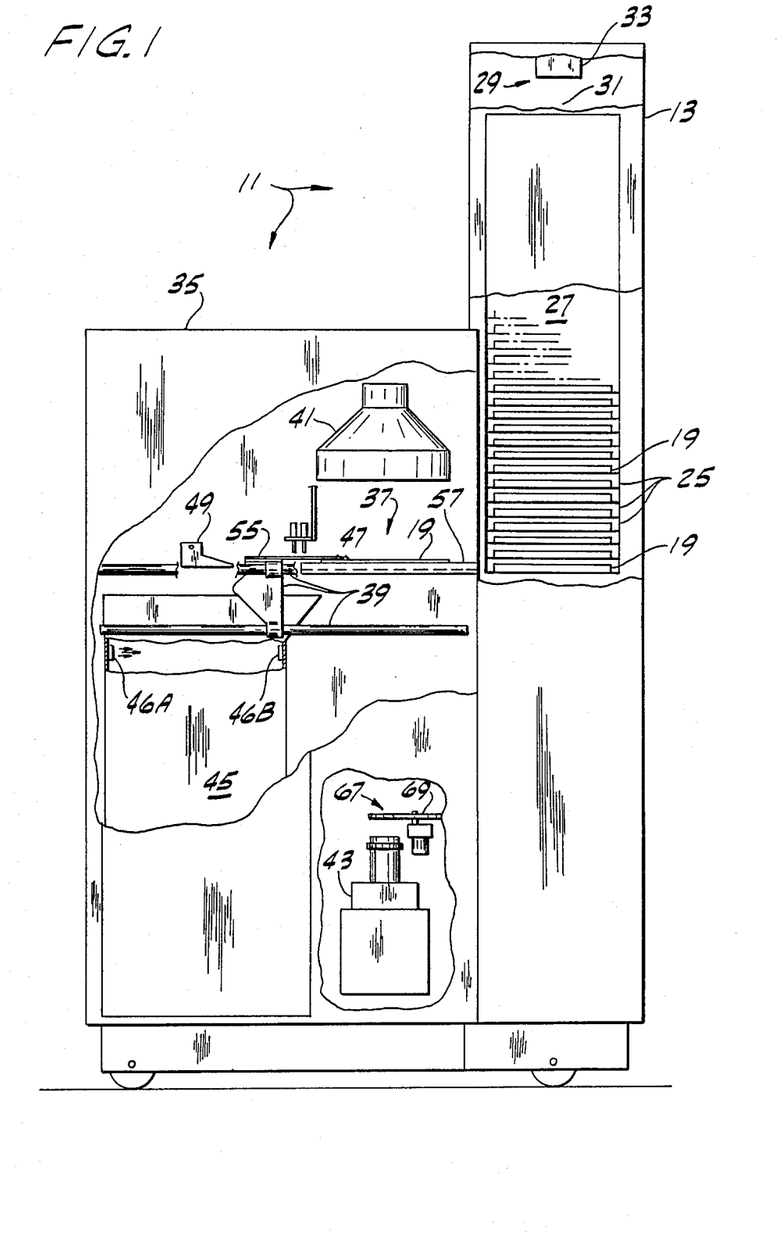
FIG. 1 is a front elevation, with parts broken away for clarity, of microbiological testing apparatus of the present invention.
Figure 10:
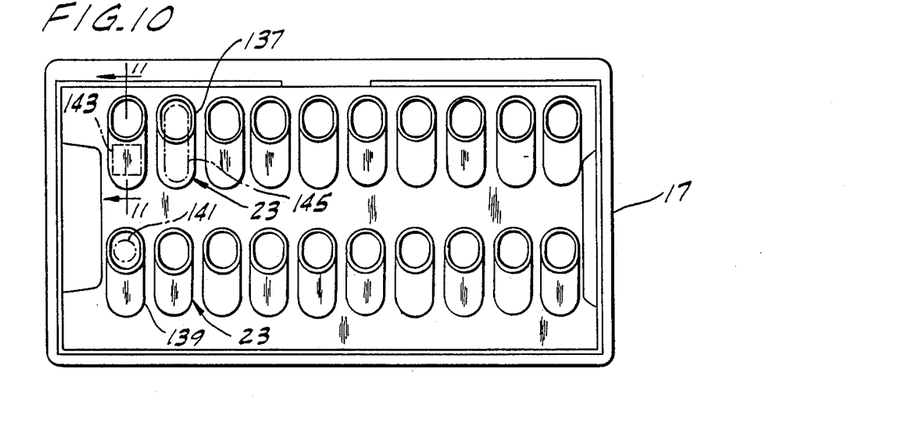
FIG. 10 is a top plan of an identification tray suitable for use with the apparatus of the present invention.
Figures 11, 12:
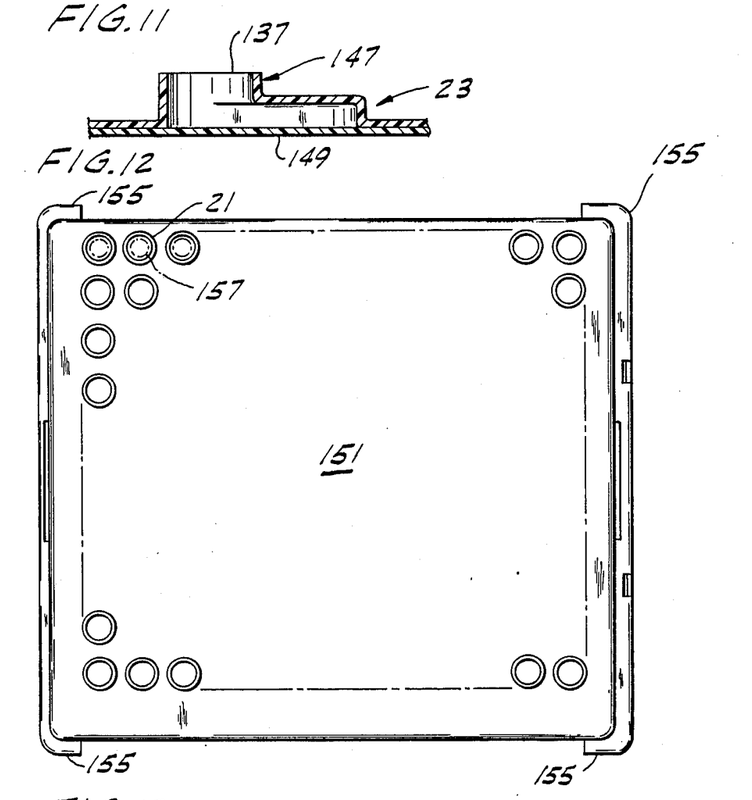
FIG. 11 is a sectional view taken along line 11—11 of FIG. 10.
FIG. 12 is a top plan of a susceptibility tray suitable for use with the apparatus of the present invention.

Referring now to FIG. 1, there is shown an automated microbiological apparatus 11 of the present invention which includes an incubation chamber 13 for incubating a plurality of microbiological test trays, such as susceptibility and identification trays 15 and 17 (see FIGS. 10 and 12), carried in a common carrier 19 (FIG. 1). As shown in FIGS. 10 and 12, susceptibility trays 15 and identification trays 17 each include a plurality of wells or cupules 21 and 23 respectively arranged in rows and columns. Referring back to FIG. 1, common carriers 19 are manually placed through an access door (not shown) in a plurality of slots 25 in incubation chamber 13. Slots 25 are vertically disposed in an elevator 27 which is movable vertically in incubation chamber 13 by a belt driven screw drive 29, of which teflon coated drive screw 31 and precision stepper motor 33 are shown in FIG. 1. Elevator 27 may include, by way of example, two rows of thirty slots so that it may accomodate up to sixty common carriers 19. By means of drive 29, any one of the slots 25 may be moved to the level of the lowermost slot shown in FIG. 1 so that the common carrier 19 therein may be removed through an access port from the incubator for processing as discussed below. Temperature and humidity within incubation chamber 13 are tightly controlled by means of a number of sensors and a heater (not shown) and the humidifier discussed below.

More particularly, apparatus 11 also includes a housing 35 in communication via the access port with the interior of incubation chamber 13. Housing 35 houses an inspection station 37 and means 39 for transporting common carriers from slots 25 through the access port to the inspection station 37 and beyond as described below. A light source 41 is disposed above inspection station 37 and a pair of video cameras 43 are disposed below the inspection station. Alternatively, a pair of light sources may be used, one above each camera. A waste bin 45 is also provided inside housing 35 having a sensor system including a photodiode 46A and a photodetector 46B for detecting when bin 45 is full. Housing 35 also houses a dispensing head 47 for dispensing reagent into identification trays 23, and a flipper system including a pair of flipper forks 49 for removing identification trays or strips from common carriers 19.

Figure 2:
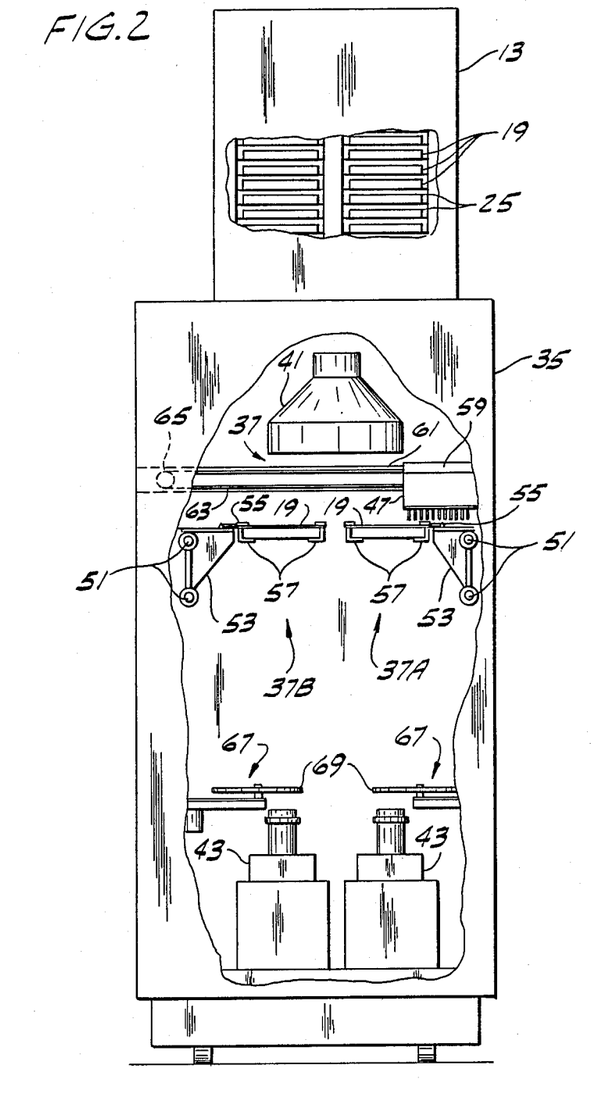
FIG. 2 is a side elevation with parts broken away of the apparatus of FIG. 1.

Turning to FIG. 2, the two rows of slots 25 in elevator 27 are seen to be disposed side by side in incubation chamber 13. Carrier transporting means 39 includes a pair of tracks 51 upon each of which ride a separate motor driven carriage 53. Each carriage 53 carries a generally L-shaped rod 55 which is movable into a corresponding recess (see FIG. 4) in common carrier 19 to move any desired carrier from its slot 25 in the incubation chamber through one of the pair of access ports 56 to inspection station 37. Carriers 19 are moved from their slots to the inspection station along a second pair of tracks 57.

Dispensing head 47 which is disposed above tracks 57 on the opposite side of the inspection station 37 from incubation chamber 13, is carried by a carriage 59 along a track 61 by a belt drive 63 including a belt drive stepper motor 65. More particularly, dispensing head 47 is movable between the extreme position shown above the rightmost track 57 to a corresponding position generally to the left of the leftmost track 57 so that any reagent may be dispensed into any cupule of the identification tray of a common carrier on either track.

Although there are a pair of tracks 57 and a pair of cameras 43, it is possibleuse a single light source 41 so long as cool and even illumation of the inspection area is achieved. It has been found that a cold cathode grid lamp equipped with a diffuser plate provides such illumination. Alternatively, a pair of such lamps equipped with diffuser plates may be used. For convenience, the inspection station can be divided into left and right halves 37A and 37B, respectively. Below inspection station 37A and between that inspection station and the corresponding camera 43 is a set of filters 67 suitably mounted for moving any of a plurality of filters to cover the field of view of camera 43. A similar set of filters is provided between inspection station 37B and rightmost camera 43. These filters can be mounted, for example, on a wheel 69 which is rotatable about its axis by a motor 71 so that the desired filter can be rotated into place as necessary. The filters can include color separation filters, neutral density filters, and calibration devices. The placement of cameras 43 and filter wheels 69 is selected so that the largest tray likely to be encountered (e.g., a susceptibility tray) lies completely within the viewing field of the camera, and requires no further motion once it is positioned within the viewing field. Camera lens and camera to tray distance are optimized to maximize the size of the tray in the field and minimize optical distortion.

Figure 3:
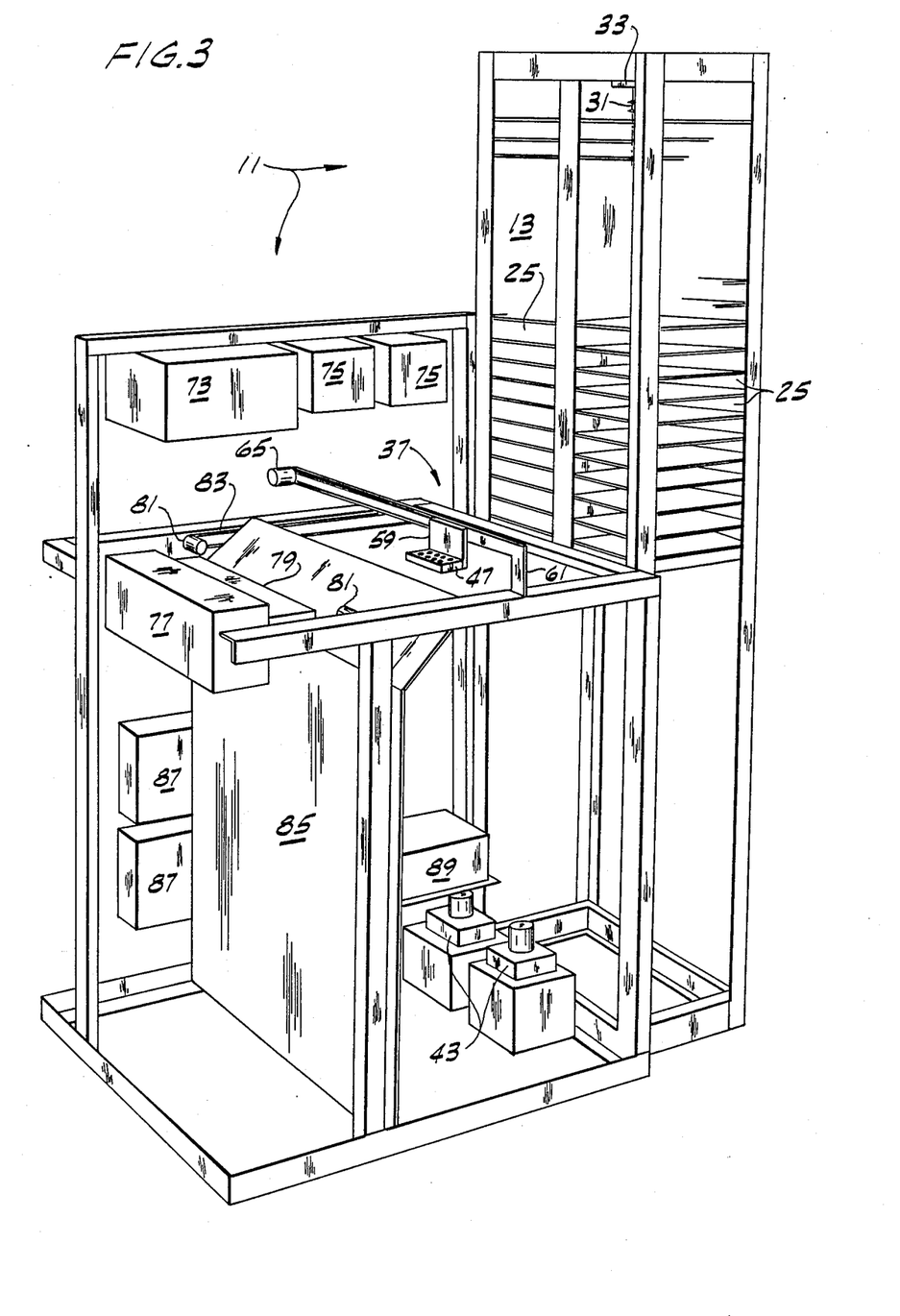
FIG. 3 is a schematic of the internal components of the apparatus of FIG. 1.

Turning now to FIG. 3, in addition to the components of apparatus 11 mentioned above there is shown a signal processing and controlling unit 73 for processing the images from cameras 43 and controlling the various functions of apparatus 11. The signal processing part of unit 73 may include image processors such as those under the trade designation System 20,000H by Unitron imagetek Systems of Plainview, New York; under the trade designation IP-512 by Imaging Technology, Inc. of Woburn, Massachusetts; under the trade designation Model 1000 by Image Technology Corporation of Deer Park, New York; under the trade designation Scan 78/99 by Eikonix corporation of Bedford, Massachusetts; or under the trade designation Model 109RM by LogE/Spatial Data Systems of Goleta, California. Signal processing and controlling unit 73 not only analyses the images from cameras 43 but also, in the manner described below, determines from that analysis a partial test result for each well in a tray and a total test result or results for each tray. Immediately to the right of the signal processing and controlling unit 73 are shown two temperature controllers 75 for controlling the temperature inside apparatus 11 and particularly the temperature inside incubation chamber 13. Below signal processing and controlling unit 73 is a reservoir 77 which contains a plurality of (e.g., twenty) reagents as needed for dispensing into identification trays 17. Pumping of reagent from the reservoir to the dispensing head 47 is controlled by a set of reagent pumps or solenoids 79. To the right of reagent solenoids 79 and suitably mounted to opposite sides of the frame of apparatus 11 are a pair of precision stepper motors 81 for driving the common carrier carriages 53. More specifically, motors 81 each are operatively connected to a belt drive 83 to drive the corresponding carriage 53 along its track 51 as necessary to move common carriers from the incubation chamber to the inspection station and to the area beneath the dispensing head 47 as necessary. A barrier or bulkhead 85 is provided generally to the left of dispensing head 47 and inspection station 37 in FIG. 3 to isolate waste bin 45 from the inspection station. Bulkhead 85 includes an inclined plane directly below dispensing head 47 so that wasted reagent (such as might appear during priming of the dispensing head) is directed into waste bin 45. A plurality of motor control drives 87 are provided to control the energization of motors 81 for the common carrier drive, of motor 33 for the elevator drive, of motor 65 for the dispensing head drive, and of motors 71 for the filter wheels. As will become apparent, signal processing and controlling unit 73 includes control circuitry for controlling the operation of apparatus 11 and in particular for controlling motor drives 87 to move the various components of the apparatus in a coordinated fashion as described below. For example, unit 73 may include a microcomputer suitably programmed to control the apparatus. Alternatively, hardwired circuitry could be provided to perform the same function. A humidifier 89 is also provided to control the humidity in apparatus 11 and particularly the humidity in incubation chamber 13.

Figure 4:
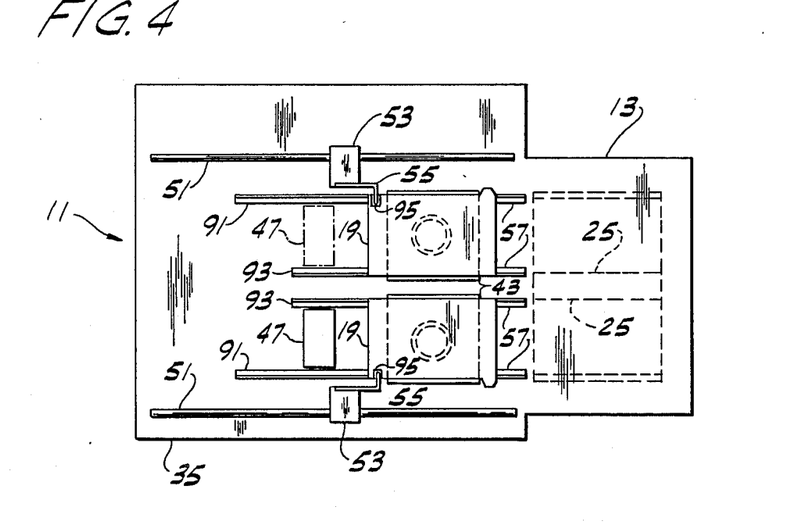
FIG. 4 is a top plan, with parts broken away for clarity, of the apparatus of FIG. 1.

Turning now to FIG. 4, each track 57 is seen to include a pair of rails 91 and 93 extending from the access ports adjacent incubation chamber 13 past the position of dispensing head 47. Rail 91 of each track extends beyond rail 93 to facilitate the disposal of carrier 19. Tracks 51 also extend generally from incubation chamber 13 generally to the opposite side of apparatus 11. Each common carrier includes a recess 95 in which a puller or grabber rod 55 may loosely rest to tow desired common carrier 19 from its corresponding slot 25 in the incubation chamber to the position shown in FIG. 4 at the inspection station. By moving the appropriate carriage 53 further to the left as seen in FIG. 4, common carrier 19 may be moved underneath the dispensing head 47. And, if desired, further motion of carriage 53 to the left in FIG. 4 results in the common carrier falling off the end of rail 93 directly into waste bin 45.

Common carrier 19 (shown in more detail in FIG. 5) includes a generally rectangular frame 97 having a cross-bar 99 extending thereacross to define two central openings 101 and 103. Opening 101 is sized to receive an identification tray such as shown in FIG. 10 while opening 103 is sized to hold one or more susceptibility trays 15 as shown in FIG. 12. A ledge 105 about one-half way down in opening 101 along the perimeter thereof is provided to support an identification tray 17 in central opening 101. A pair of notches 107 are provided in the front wall of frame 97 to allow the tines 109 of fork 49 to remove an identification tray from central opening 101. Notches 107 extend below ledge 105 and the tines 109 are sloped rearwardly so that as carrier 19 is moved to the position of fork 49, the tines pass under the identification tray and lift it free of carrier 19. Between both forks 49 extends a striker flange 111 disposed generally at the top rear of the forks.

Figure 5:
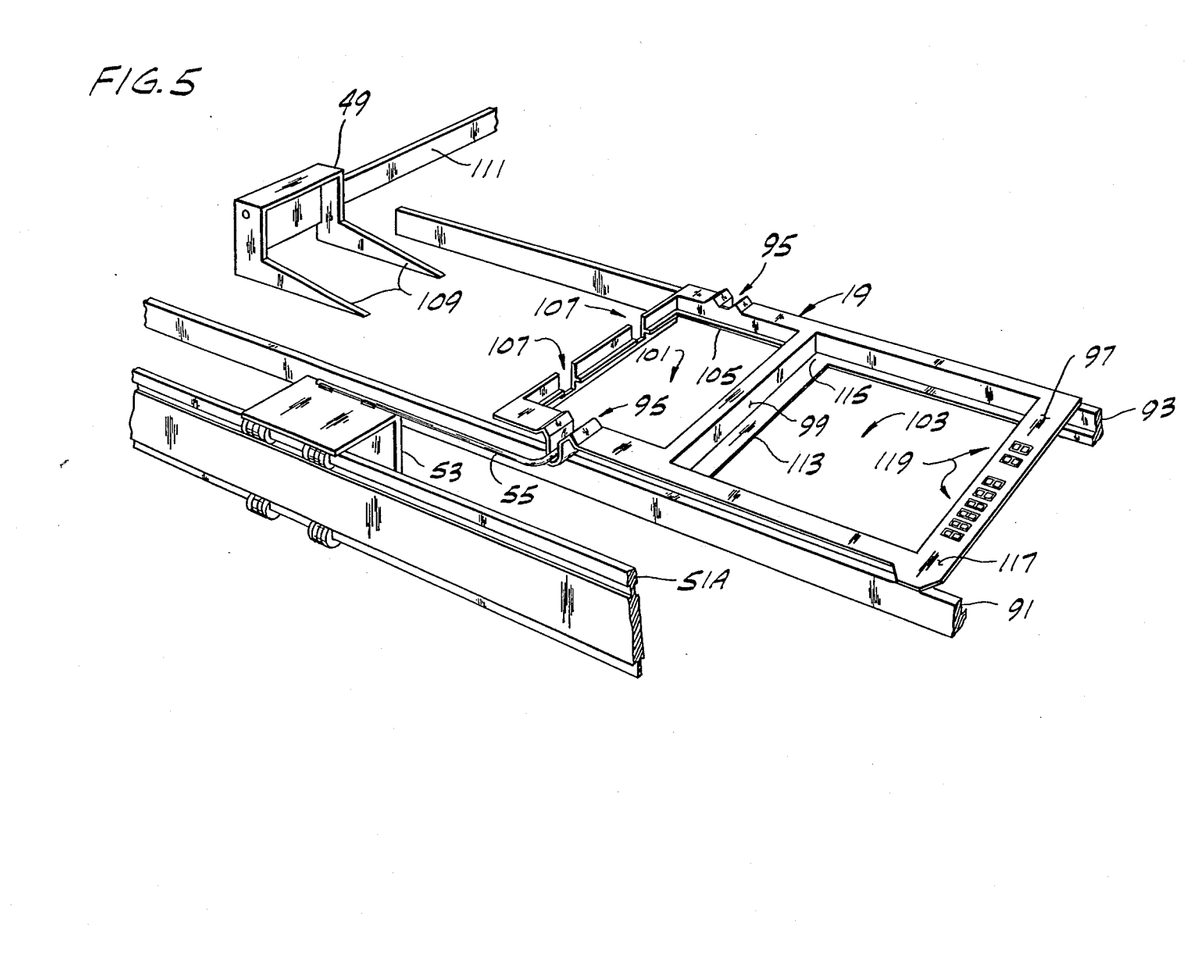
FIG. 5 is a perspective illustrating a tray carrier and transporting means of the present invention.

Similarly, central opening 103 includes a ledge 113 for supporting one or more susceptibility trays 15. A pair of positioning posts 115 extend up from ledge 113 to accurately and securely position a susceptibility tray in central opening 103. Common carrier 19 also includes an offset 117 extending generally out from the frame at the lower right-hand corner thereof as shown in FIG. 5 for the purpose of insuring that common carrier 19 is loaded into incubation chamber 13 with the proper orientation. Chamber 13 includes corresponding structure (not shown) which prevents the carrier from being inserted into a slot 25 if it is turned the wrong way. Also on the rightmost part of frame 97 is a set of recesses 119, each in the shape of the numeral "8" which are provided to accurately define the position at which the user writes down the patient or specimen identification information for the trays carried by that particular carrier 19. Recesses 119 also insure that the identification number can be easily read by the image processing system of the present invention. FIG. 5 also illustrates one of a number of alternative embodiments (this one labelled 51A) of track 51.

Figure 6:
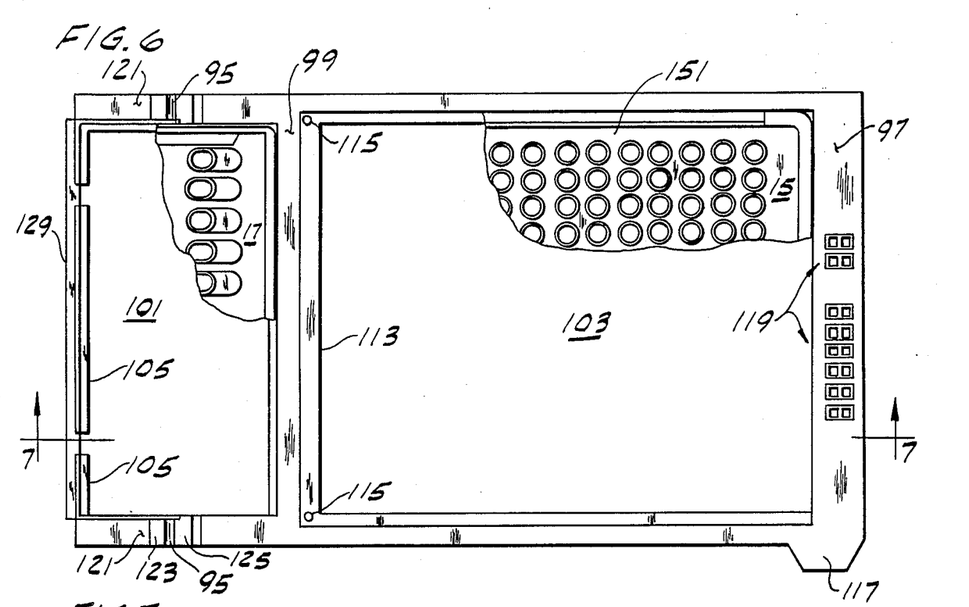
FIG. 6 is a top plan of the tray carrier of FIG. 5 showing portions of identification and susceptibility trays in place.
Figure 7:
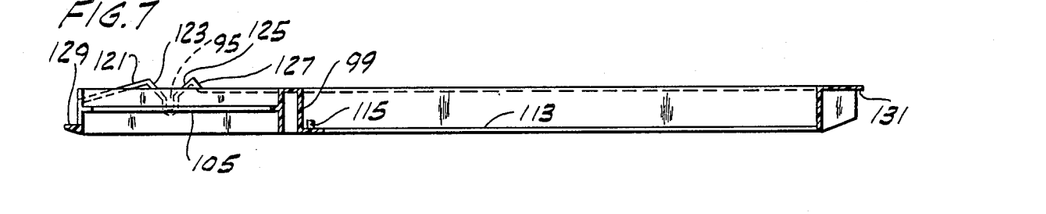
FIG. 7 is a sectional view taken along line 7—7 of FIG. 6.

Looking now at FIGS. 6 and 7, frame 97 is seen to include a upwardly sloping front surface 121 up which rod 55 may slide if necessary (although it is preferred that such sliding not be necessary) as it is pushed into a slot 25 in incubation chamber 13. At the uppermost extent of ramp 121, a descending ramp 123 is provided which terminates in recess 95. Another upwardly extending ramp 125 is disposed at the rear of recess 95 and it terminates in a descending ramp 127 which descends to the general level of the top of frame 97. Also shown in FIG. 6 is a portion of susceptibility tray 15 in central opening 103 and a portion of identification tray 17 in central opening 101. Frame 97 also includes a front lip 129 disposed generally at the bottom of the frame. In FIG. 7, cross-bar 99 is seen to be generally C-shaped and number recesses 119 are seen to be positioned on the upper surface of a ledge 131 of carrier 19.

Figure 8:
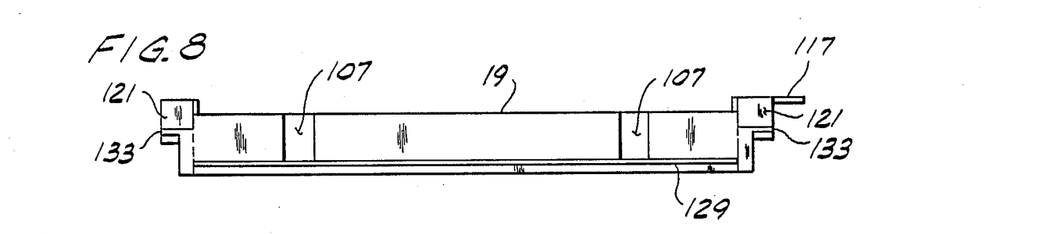
FIG. 8 is a front elevation of the carrier of FIG. 6.
Figure 9:
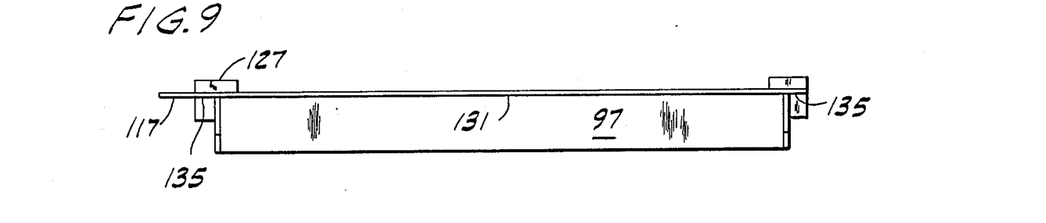
FIG. 9 is a rear elevation of the carrier of FIG. 6.

Frame 97 (FIG. 8) has a pair of shoulders 133 at the front which extend out from the body of the carrier and provide the front surface from which ramp 121 inclines. Similarly, the rear view of carrier 19 (FIG. 9) reveals that frame 97 also defines a surface or shoulder 135 for supporting carrier 19 as it is moved along tracks 57.

An identification tray 17 (FIG. 10) suitable for being carried in central opening 101 of carrier 19 includes a pair of rows of wells or cupules 23 arranged in columns. The cupules may contain different reagents, some of which are dispensed therein by dispensing head 47, for identifying various microorganisms. Each cupule includes a generally circular open or aerobic portion 137 and a generally closed or anaerobic portion 139 in fluid communication with portion 137. Cupules 23 are in fact chambers where reactions take place between the reagent therein and the particular sample which has been innoculated into each cupule, which reactions can identify the particular microorganism present in the sample. However, not each reaction has the same result. In some reactions, a result would appear only in section 137, which is exposed to air. Other reactions might occur only in the anaerobic portion 139 of the cupule. Still other reactions might be present in both parts of the cupule. Such reactions can involve color change, turbidity change, or the formation of a product of some generally predetermined shape. Thus, for any given cupule it may not be necessary to analyze the entire cupule. It may be that an area of interest 141 in section 137 would be the only area of that cupule whose image would need to be processed. Similarly, for other reactions an area of interest 143 in the closed section 139 of cupule 23 may be all that is required. In still other reactions, an area of interest 145 extending through both the aerobic and anaerobic sections of the cupule may be needed. Other possible areas of interest in terms of shape, placement, and size could be needed or desired depending upon the reactions involved.

Cupule 23 (FIG. 11) includes a raised neck 147 in the area of section 137 and is preferably formed out of a single layer of transparent, relatively rigid plastic material. The base of cupule 23 is formed by a transparent substrate 149 common to all the cupules.

Figure 13:
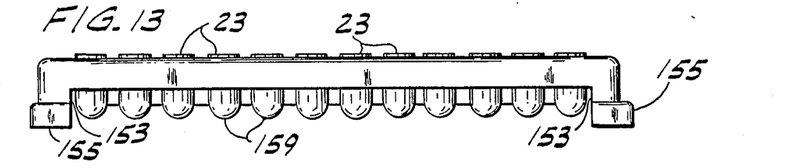
FIG. 13 is an elevation of the tray of FIG. 12.

Turning to FIG. 12, susceptibility tray 15 includes a large number of wells 21 arranged in rows and columns. Wells 21 are disposed in a relatively flat sheet 151 of rigid plastic material having depending shoulders 153 (FIG. 13). Along two sides, shoulder 153 is extended outwardly and downwardly in a flange 155 having a wall thickness sufficiently small to fit between positioning post 115 and frame 97 of the carrier (FIG. 6). An area of interest 157 for any of wells 21 could be generally of the same outline as the well itself, since in susceptibility testing one is normally looking for a turbidity change which will be present throughout the entire well. Other areas of interest could, of course, be used. Wells 21 (FIG. 13) have a convex bottom surface 159 which tends to magnify the contents of well 23 when that well is viewed from below as seen in FIG. 13.

Figure 14:
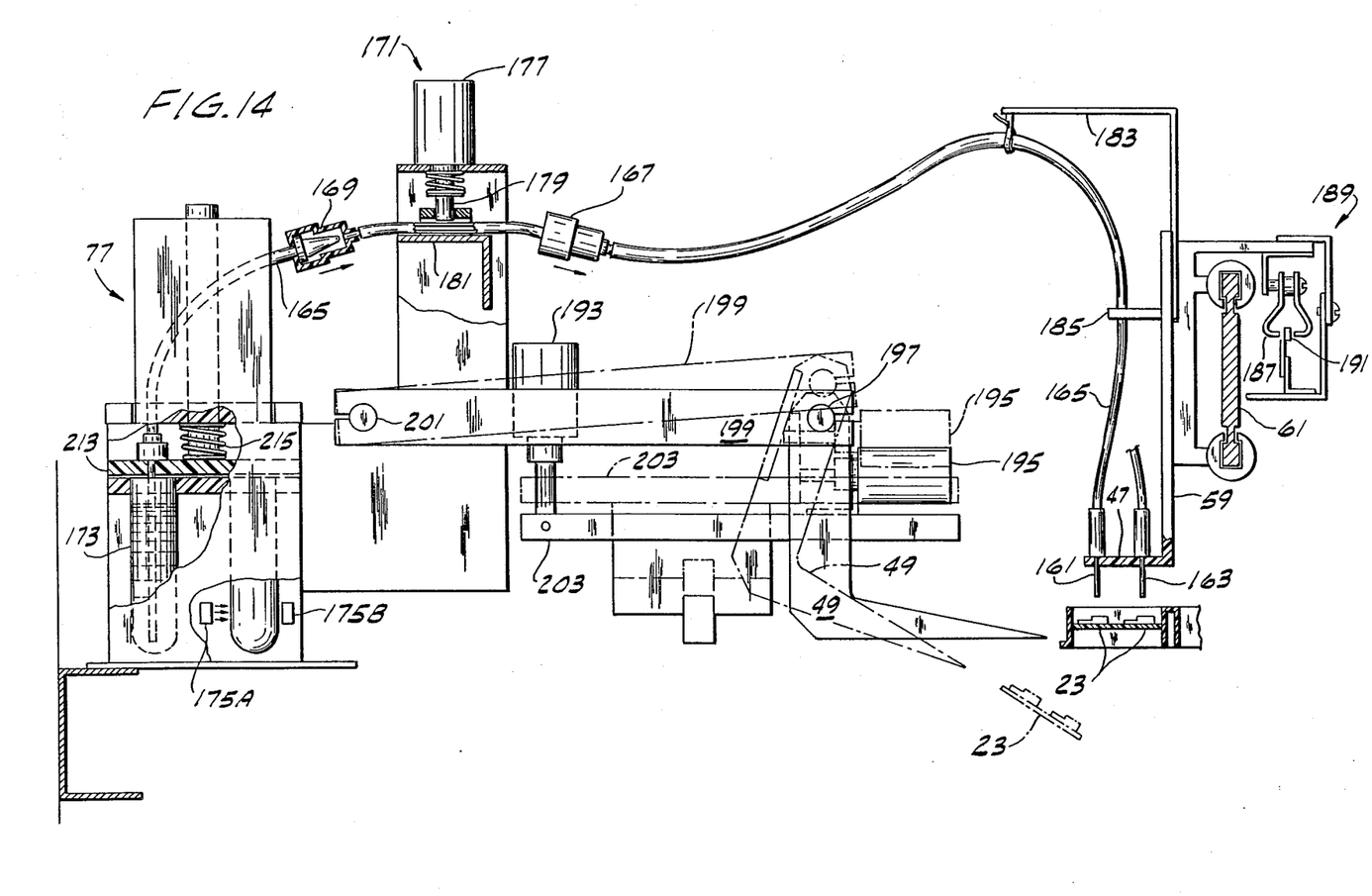
FIG. 14 is a schematic illustrating the reagent handling and identification tray removal subassemblies of the apparatus of FIG. 1.

The reagent dispensing and identification tray removing features of the present invention are illustrated in more detail in FIG. 14. Dispensing head 47 includes two rows of reagent dispensing nozzles 161 and 163 for dispensing reagent into cupules 23. The identification tray can be positioned by rod 55 as described above so that the aerobic portions of cupules 23 are disposed directly underneath nozzles 161 and 163. Each nozzle of each row is connected by a flexible tube 165 (only two of which are shown) through a pair of one-way valves 167 and 169 and a pumping mechanism 171 to a bottle 173 of the appropriate reagent. Assuming there are twenty nozzles, up to twenty different reagents may be dispensed into any of the cupules by appropriate placement of dispensing head 47.

Each reagent bottle 173 may have associated therewith a sensor 175 for detecting when the reagent bottle is effectively empty. Such a sensor 175 is illustrated in FIG. 14 as a photosensor having a light source 175A and a photodetector 175B. Other sensors could of course be used. Assuming reagent is present in reagent bottle 173, it is pumped by a pumping mechanism 171 (each tube and associated reagent has its own pumping mechanism 171) through tube 165 to the corresponding nozzle 161 or 163. Pumping mechanism 171 includes a solenoid 177 with a plunger 179 disposed on one side of tube 165 while on the other side of tube 165 is a flange 181 against which tube 165 can be compressed by plunger 179 when solenoid 177 is energized. The operation of solenoid 177 is, of course, under the control of control circuitry 73. Each time solenoid 177 is energized it forces a predetermined amount of reagent out of tube 165. Note should be taken that tube 165 is normally open and that dispensing of reagent occurs only when the tube is closed or compressed by solenoid 177. This feature is made possible by the presence of the two one-way valves 167 and 169 which may be conventional duck-bill valves. As a result of this arrangement, an accurate amount of reagent is dispensed with each operation of solenoid 177 and drops from tube 165 are prevented from falling from the dispensing head after the solenoid is deenergized.

Each tube 165 is suspended above fork 49 by a strap 183 secured to carriage 59. Carriage 59 also includes a spacer 185 to hold tubes 165 secure as dispensing head 47 is moved. Carriage 59 also suitably supports a magnet 187 which moves along with carriage 159 as it is moved along track 61. Disposed adjacent track 61 but fixed with respect thereto is a sensor support 189 which fixably support a series of Hall-effect sensors 191 (only one of which is shown) which determine when the dispensing head 47 is properly positioned above an identification tray (assuming the identification tray is in the position shown in FIG. 14) to dispense the desired reagent into the desired cupule.

The system for removing and dumping identification trays includes not only fork 49 but also a pair of solenoids 193 and 195. Fork 49 is rotatably mounted on a rod 197 extending therethrough at its upper end. Rod 197 defines an axis about which fork 49 is pivotable. Rod 197 is fixedly secured to a rigid beam 199 of a pair of generally parallel beams 199 at one end of said beams. The other end of beams 199 is pivotably mounted on a second rod 201.

The plunger of solenoid 193 is fixedly connected to one end of a lifter bar 203 which has solenoid 195 secured to the other end thereof. Lifter bar 203 is constrained to move only vertically, so that when solenoid 193 is energized, it raises lifter bar 203 and solenoid 195 to the positions shown in phantom in FIG. 14. This also causes fork 49 to be pushed upwardly without rotation of the fork, which results in beam 199 pivoting around rod 201 to the position shown in phantom in FIG. 14. If the tines of fork 49 are under an identification tray at the time solenoid 193 is energized, energization of that solenoid will therefore result in the fork and the identification tray being moved upward an amount sufficient to lift the tray free of carrier 19. Subsequent energization of solenoid 195 causes its plunger to strike striker flange 111 between the forks, forcing both forks to pivot about the axis of rod 197 to the position shown in phantom in FIG. 14. In this position, identification tray 17 falls free into waste bin 45. Thus, to remove an identification tray from a common carrier 19, the tray is first moved by tray transporting means 39 to the position somewhat to the left of that shown in FIG. 14 in which the tines of fork 49 enter through the notches in the front wall of common carrier 19 and pass under identification tray 17. Once the common carrier is in this position, solenoid 193 is energized which lifts the identification tray free of the carrier. Then carrier transporting means 39 is energized to move the common carrier back to the position shown in FIG. 14 or beyond and solenoid 195 is energized to discard the identification tray as shown in FIG. 14.

Turning now to FIG. 15, reagent reservoir 77 is seen to include a mounting plate 205 slidingly disposed in a pair of end plates 207 (only one of which is shown). A stationary alignment plate 209 is disposed directly above mounting plate 205 and contains a plurality of openings therethrough centered directly above the reagent bottles 173. A movable top plate 211 is also slidingly secured to end plates 207. Top plate 211 has a plurality of draw tubes 213 secured thereto which fit through the openings in alignment plate 209 for passage into reagent bottles 173. Each draw tube 213 is suitably connected to its corresponding tube 165. This particular construction of reagent reservoir 77 allows the reagent bottles to be removed as a module or unit for replacement, thereby minimizing downtime of the apparatus.

This removal and replacement is easily accomplished by moving top plate 211 up with respect to end plates 207 to the position shown in FIG. 15 and then sliding reagent mounting plate 205 along with the reagent bottles to left as shown in FIG. 15 to remove the entire module from the reservoir. A filled reagent module can then be inserted in its place and top plate 211 moved back down to the position shown generally in FIG. 14. A spring 215 is provided to bias top plate 211 upwardly and to cushion the relative motion between top plate 211 and the reagent module. In addition, a latch 217 is provided to latch the top plate in the operating position shown in FIG. 14.

Turning now to FIG. 16, a slot 25 in incubation chamber 13 is shown with a photoelectric sensor consisting of a light source such a photodiode 219 on one side of the slot and a photodetector 221 on the other side of the slot. When a common carrier 19 is present in the slot as shown in phantom in FIG. 16, the light from photodiode 219 is prevented from reaching photodetector 221, but when the common carrier is not present the light from the photodiode can fall on photodetector 221. Thus, the combination of photodiode 219 and photodetector 221 comprise a sensor for sensing the presence of a common carrier in the particular slot 25 associated with that photodiode and photodetector. Each of the 60 slots has a photodiode/photodetector combination so that the control circuitry can determine at all times which slots contain common carriers and which slots are empty.

The control circuitry must not only know which slots are empty but also must know the position of elevator 27 in incubation chamber 13 since common carriers can be removed from the incubation chamber only when there particular slot is at the level of the corresponding access port as shown in FIG. 2. The control circuitry determines the position of the elevator by means of a series of 30 Hall-effect sensors 223 (FIG. 18) fixedly secured to a flange 225 which is stationary with respect to the housing of incubation chamber 13. A magnet 227 is suitably mounted on a member 229 which moves with elevator 27. There is a sensor 223 corresponding to each of the slots 25 in a row so that as elevator 27 is raised or lowered the Hall-effect sensors detect the magnet as the magnet is moved each slot position. In this way the control circuitry can accurately determine which slot is present at the access ports, so that its common carrier can be removed from the incubation chamber by the carrier transporting means 39. The use of precision stepper motor 33 also helps provide accurate control of the position of the elevator.

Similarly, a series of Hall-effect sensors 231 are fixedly secured which respect to track 57 and represent possible desired positions of the common carrier. Such desired positions of the common carrier could include at the inspection station, at the dispensing head and the position at which the identification tray is removed by fork 49 from the carrier. A magnet 233 is suitably mounted to a flange 235 which moves with carrier 53. The position of magnet 233 thus accurately represents the actual position of the common carrier. Accurate positioning of the carriers is also achieved by the use of precision stepper motors 81.

The operation of apparatus 11 is as follows:

The user of apparatus 11 would first innoculate identification tray 17 and susceptibility tray 15 in the ordinary manner. These trays could be placed in common carrier 19 either before or after innoculation with the sample to be tested. The user would write an identifying number in recesses 119 on the common carrier and insert the common carrier into an empty slot 25 in incubation chamber 13. To insert the carrier into an empty slot the user must open the access door (not shown). All doors of apparatus 11 are normally locked and are undertheir control of controlling unit 73. To open the elevator access door, the user would press a door request switch. In response unit 73 would unlatch all doors as soon as any critical opertion occurring at the time was completed. Such critical operations would include any movement of transporting means 39, the reading of any tray by the video cameras, the addition of reagent to the cupules, and the development of color in the cupules. This latching feature, implemented in the software of unite 73, prevents operator errors such as the insertion of a carrier into a slot whose occupant is at the inspection station, the changing of a reagent which is about to be dispensed, or the removing of the waste bin(biohazard bag) at a point when a carrier is about to be discarded.

Control circuitry 73 by means of the photodiode 219 and photodetector 221 associated with the slot in which the carrier was just inserted would determine that a common carrier has been inserted into that particular slot 25. The control circuitry thereupon directs motor 33 to drive elevator 27 to the proper level so that the newly inserted tray 19 may be removed from slot 25 and taken to inspection station 37. Once the desired slot reaches the access port at which it can be removed and taken to the inspection station, it is indexed down by stepper motor 33 one-half step so that the hook or rod of the carrier transporting means can be moved into the incubation chamber and placed directly over groove 95. The elevator is then moved one-half step upwards so that the groove in the carrier is engaged by the hook of the transporting means. The hook is then moved to the left as shown in FIG. 1, thereby towing the desired common carrier along tracks 57 to the inspection station. Once the carrier reaches the inspection station as precisely revealed by the appropriate magnet 231 and Hall-effect sensor 233, the number written on the tray is read. This reading is accomplished by processing the image of the tray made by camera 43. More specifically, the control circuitry and image processing circuitry is programmed so that in this mode of operation its only areas of interest correspond to the line segments of recesses 119. The image processing system considers only those particular line segments. By determining whether a particular line segment has been written on (by examining the light level coming through that particular segment) it can readily determine the particular identification number written in recesses 119. In a similar fashion, the control circuitry can identify the particular type of identification and susceptibility trays present in common carrier 19 by examining the area of interest corresponding to a product code for that particular tray. For example, the susceptibility tray shown in FIG. 12 has the product identification ledgend "MIC" stamped thereupon. By examining areas of interest corresponding to the various segments which make up this legend, control circuitry 73 can identify the type of tray. The various kinds of identification trays can be similarly identified. After identification of the trays and the speciment number, the carrier is returned to its slot by transporting means 39 and the elevator is indexed down one-half step. Moving the elevator down one-half step results in rod 55 being freed from slot 95 in the carrier. Rod 55 is then moved out of the incubation chamber and the elevator is indexed back up.

To process the images of the numbers written in recesses 119 and the images in the wells and cupules as discussed below, image processing and controlling unit 73 requires uniformity in lighting over the inspection station 37. In part, this is acheived by the particular light source 41 described above. In addition, the image processor also has recorded the background light level at each point or pixel in the areas of interest, which will account for any variability in the light source. In addition, in reading the results of various trays, it may be desirable at times to compare the result of the image processing for any particular well after incubation with that processed image taken generally before incubation occurs. For this reason, at some initial time T-zero such as thirty minutes after the carrier is inserted into the incubation chamber, the common carrier it is desired to test is again moved by the elevator to the corresponding access port and from there moved by transporting means 39 to the inspection station. Because of the presence of the position sensing mechanism of FIG. 18, the tray is accurately and repeatably positioned in the same position at inspection station 37 each time. Such accuracy is also assured by the use of a stepper motor to drive transporting means 39. Image processing and controlling unit 73 thereupon begins taking baseline readings for each of the cupules and wells contained in the trays and carrier 19 at the inspection station. The image processing and controlling unit 73 looks at each cupule and well sequentially and more particularly considers the image only within the area of interest for each particular cupule and well. Unit 73 can be programmed to set the particular size, shape and placement of the areas of interest so that different trays with different tests may be read with the same apparatus 11. Once the apparatus identifies the particular type of tray as described above, it then sequentially inspects the areas of interest that have been previously defined for that particular tray. For example, the identification tray shown in FIG. 10 has three exemplary areas of interest shown in three different cupules. Other trays might have areas of interest of different sizes and/or shapes and these areas of interest may or may not vary from cupule to cupule for a particular tray. Image processing and controlling unit 73 thus looks at the area of interest for one cupule and records the results, then looks at the area of interest for the next cupule and records the results, and so on until all the cupules have been examined. The wells of susceptibility tray 15 (FIG. 12) are sequentially examined in a similar manner at the appropriate time.

The output of video camera 43 is a voltage for each picture element or pixel in the areas of interest. The image processing and controlling unit is programmed to count the number of pixels in a given area of interest whose associated voltage exceeds a particular threshold. For example, in an imaging system capable of resolving 256 gray levels from black to white, where black is full voltage and white is zero voltage, there would be associated with each area of interest a threshold voltage value which discriminates between a positive and negative result for that particular well. The baseline measurements being taken, therefore, represent the number of pixels in each area of interest that have an associated voltage greater than the predetermined threshold. This baseline value is used later by the image processing and controlling unit to determine the actual change in a well after incubation period. After the baseline values are taken, the carrier is returned to the incubation chamber as described before and incubation of the trays is resumed.

Image processing and controlling unit 73 has preprogrammed information concerning the incubation times for the various types of trays which may be used therewith. Since the unit has identified the particular trays as to type in any carrier as described above, it can and does set the incubation period for each tray. Typical incubation time might be five hours for an identification tray and 24 hours for a susceptibility tray. After the five hours of incubation for a particular identification tray have expired, the common carrier carrying that particular tray is again moved to the position in which the transporting means 39 can remove that carrier from the incubation chamber. If in fact the identification tray is one of those which requires the addition of reagent from dispensing head 47 after incubation, controller 73 then moves the common carrier by means of transporting means 49 to the position shown in FIG. 14. If it is not already present, the dispensing head 47 is moved under the control of controller 73 to the proper position over identification tray 17. It may be that more than one reagent is desired in any given cupule of identification of tray 17. This is accomplished by positioning the dispensing nozzle corresponding to one of the desired reagents above the cupule, pumping the desired reagent into the cupule, and then moving the dispensing head again to position the dispensing nozzle of the desired second reagent over the cupule. The second reagent is then pumped into the cupule as well. Use of the stepper motor and Hall-sensors as discussed above allows this precise placement of dispensing head 47. After dispensing any desired reagents into the proper cupules of identification tray 17 and waiting an appropriate time for any reaction(s) to occur, controller 73 causes carrier 19 to be moved by transporting means 39 back to the inspection station. For certain tests, it may be necessary to move the identification tray back to the inspection station after reagent is added to each cupule. For others, it may be possible to wait until reagents have been added to all cupules before the carrier is moved to the inspection station for reading. At the inspection station, the image processing and controlling unit again examines the areas of interest in each desired cupule of the identification tray. Because the results of some identification tests may involve color changes, controller unit 73 may control the appropriate filter wheel 69 to examine a particular cupule one or more times using one or more filters to determine if that color change has in fact taken place. For each cupule and more specifically for each area of interest within a cupule, the image processing and controlling unit determines the number of pixels in that area of interest which have an associated voltage exceeding the predetermined threshold for that area of interest. If that number pixels exceeds a predetermined number, a positive result is assigned to that cupule. Alternatively, a positive result could be assigned to a well or cupule if the average gray level (voltage) of the area of interest exceeded some predetermined threshold. These cupule results are called binary partial results since they represent only whether a particular reaction has taken place in a particular cupule. The image processing and controlling unit then analyzes the binary partial results from the cupules to determine the possible identity of the microorganism in the sample. This determination is made by comparing the partial binary results from this particular identification tray with prerecorded patterns of results for such identification trays. If the pattern of binary partial results does not correspond to a known pattern, i.e., if the pattern of results if illogical in some way, the image processing and controlling unit causes the carrier to be returned to the elevator and a warning message to be displayed to the user that particular identification tray should be read manually. On the other hand, if the pattern of results for the identification tray is logical, the probable identification of the microorganism is recorded by image processing and controlling unit 73 and the common carrier is moved to the position where the fork can remove the identification tray and dispose of it into waste bin 45. The common carrier with its susceptibility tray still intact is then returned to the incubation chamber for additional incubation.

After the incubation of the susceptibility tray is complete, the common carrier carrying the susceptibility tray is again moved to the inspection station where it is read in a similar manner to that of the identification trays. In the case of the susceptibility tray, however, there will be a series of results which represent the various antimicrobics to which the microorganism is susceptible and the required concentration of that antimicrobic. These results are again stored by image processing and controlling unit 73. After the reading of the susceptibility tray, the transporting means 39 pulls the common carrier and susceptibility tray along its track 57 until the common carrier with the tray fall off shorter rail 39 into waste bin 45. Solenoid 193 is energized during this operation to remove fork 49 from the path of the carrier.

Thus, it is seen that apparatus 11 in a fully automated way incubates reads and disposes of identification and susceptibility trays while recording the results of those tests for later use. Other types of trays could of course be read in a similar manner by apparatus 11, including various biochemical trays and any other tray which would show a predictable reaction change in an area of interest.

In view of the above, it will be seen that the various aspects and features of the invention are acheived and other advantageous results attained. Changes, alterations, and modifications of the apparatus will be apparent to those skilled in the art and are to be considered within the spirit and scope of the invention.

What is claimed is:

1. The method of automatically reading results of reaction tests between agents and samples in wells of microbiological test trays and strips such as susceptibility trays and identifiction trays, comprising the steps of:
    making an image with a video camera of a tray having samples and agents together in the wells of the tray for at least a predetermined time;
    then electronically analyzing only predetermined areas of interest in the image made by the camera, which areas of interest are substantially within the peripheries of the tray wells in the image;
    for each well of interest, electronically determining whether an area of interest therein has an associated value that exceeds a predetermined threshold for that area of interest; and
    electronically assigning a binary partial result to each well based upon whether the predetermined threshold for each corresponding area of interest is exceeded.

2. The method as set forth in claim 1 wherein the areas of interest for at least two different wells in a tray differ in shape.

3. The method as set forth in claim 1 wherein at least two wells of interest have different predetermined thresholds.

4. The method as set forth in claim 1 including the further step of interposing at least one optical filter between the tray to be read and the video camera so that the binary partial result for at least one well of interest may represent whether a color change has occurred in said one well.

5. The method as set forth in claim 1 wherein the tray may have an identifying product symbol thereon and further including the step of electronically determining the particular type of tray present at an inspection station at a given time by processing the image of the tray generated by the video camera.

6. The method as set forth in claim 5 wherein said determining step includes electronically analyzing the image only at predetermined areas where the product symbol is located.

7. The method as set forth in claim 1 wherein the tray includes a plurality of locations for manually writing numbers thereon, and further including the step of electronically reading the plurality of locations on a tray by processing at least one predetermined area of interest in each of the plurality of locations to determine the presence of an image corresponding to a manually written number.

8. The method as set forth in claim 1 wherein said determining step includes determining if the area of interest, which includes a predetermined number of pixels, has a voltage which exceeds a predetermined voltage, and a binary partial result is assigned to each well based upon the number of pixels that exceed the predetermined voltage.

9. The method as set forth in claim 8 including the step of providing background light to enhance the image, and storing the background light level to provide a base level of light for each pixel at least in the areas of interest to account for spatial variability of the light.

10. The method as set forth in claim 1 wherein the trays are incubated for a predetermined time before being read, further including the step of reading a tray before significant incubation to determine baseline values for that tray.

11. The method as set forth in claim 10 further including the step of comparing the baseline values for each well with the values obtained after a predetermined time of incubation.

12. The method as set forth in claim 1 further including determining the identity of a microorganism in an identification tray by electronically assigning a binary partial result to each well of the identification tray.

13. The method as set forth in claim 1 further including determining the susceptibility of a microorganism in a susceptibility tray by electronically assigning a binary partial result to each well of the susceptibility tray.

14. The method as set forth in claim 1 wherein an identification tray and a susceptibility tray for a single patient are mounted on a common carrier, further including the step of reading the identification tray at a first predetermined time and storing the result, automatically discarding the identification tray, and then reading the susceptibility tray at a later, second predetermined time.

15. The method as set forth in claim 1 further including the steps of sequentially reading the wells in a tray to generate a series of binary partial results.

16. The method as set forth in claim 1 wherein the location of the predetermined areas of interest are determined through programming.

17. The method as set forth in claim 16 wherein the shape of the predetermined areas of interest are also determined through programming.

18. The method as set forth in claim 1 wherein the trays are placed in an incubator prior to reading, further including the step of electronically recording the identity and then determining the position of a tray in the incubator.

19. The method as set forth in claim 18 wherein the tray is automatically removed from the incubator and transported to an inspection station where its identity is determined, and then automatically transported back to the incubator.

20. The method as set forth in claim 1 including the further step of electronically recognizing illogical combinations of binary partial results and signalling that fact.

21. The method as set forth in claim 20 wherein a tray is normally automatically discarded after the binary partial results are read but if an illogical combination is detected the tray is retained for manual review.

22. The method of automatically reading results of reaction tests between agents and samples in wells of microbiological test trays and strips such as susceptibility trays and identification trays, comprising the steps of:

moving a tray to be read having samples and agents together in wells of the tray for at least a predetermined time to an inspection station;

electronically reading the tray at the inspection station with a video camera which remains substantially stationary with respect to the tray while the reading of the tray is occurring; and electronically processing the readings for determining test results.

* * * * *